(12) United States Patent
Takii et al.

(10) Patent No.: US 8,998,410 B2
(45) Date of Patent: Apr. 7, 2015

(54) CORNEAL ENDOTHELIAL CELL PHOTOGRAPHING APPARATUS

(75) Inventors: Michihiro Takii, Aichi (JP); Naoto Honda, Okazaki (JP)

(73) Assignee: Nidek Co., Ltd., Gamagori-shi (JP)

(*) Notice: Subject to any disclaimer, the term of this patent is extended or adjusted under 35 U.S.C. 154(b) by 49 days.

(21) Appl. No.: 13/241,385

(22) Filed: Sep. 23, 2011

(65) Prior Publication Data

US 2012/0086911 A1    Apr. 12, 2012

(30) Foreign Application Priority Data

Sep. 30, 2010  (JP) ................. 2010-223124
Aug. 31, 2011  (JP) ................. 2011-188642

(51) Int. Cl.
*A61B 3/14* (2006.01)
*A61B 3/10* (2006.01)
*A61B 3/15* (2006.01)
*A61B 3/12* (2006.01)

(52) U.S. Cl.
CPC .. *A61B 3/152* (2013.01); *A61B 3/12* (2013.01)

(58) Field of Classification Search
USPC ......... 351/200, 205, 206, 208, 222, 221, 210, 351/211, 243, 245, 239
See application file for complete search history.

(56) References Cited

U.S. PATENT DOCUMENTS 5,436,679 A * 7/1995 Ohtsuka et al. ............... 351/206

FOREIGN PATENT DOCUMENTS

| JP | 08-047482 | * | 8/1994 | ............ A61B 3/12 |
| JP | A-07-079924 | | 3/1995 | |
| JP | A-08-206080 | | 8/1996 | |
| JP | 2005-342114 | * | 12/2005 | ............ A61B 3/14 |
| JP | 2009-201981 | * | 9/2009 | ............ A61B 3/10 |

* cited by examiner

*Primary Examiner* — Stephone B Allen
*Assistant Examiner* — Brandi Thomas
(74) *Attorney, Agent, or Firm* — Oliff PLC

(57) ABSTRACT

An apparatus including: a main unit including a system for irradiating illumination light from a light source to a cornea of an eye from an oblique direction and a system for obtaining a corneal endothelial cell image by receiving reflection light from the cornea by a first imaging element; an anterior segment observation optical system including a second imaging element, the anterior segment observation optical system configured to pick up an anterior segment image of the eye by the second imaging element to observe the anterior segment image from front; a controller adapted to turn on the light source and obtain a plurality of picked-up images output from the first imaging element; and a unit adapted to detect an alignment state of the main unit with respect to the eye based on a picked-up image output from the second imaging element during obtaining of the picked-up images by the controller.

7 Claims, 8 Drawing Sheets

FIG.9

|  | RETURNING TIME (s) |
|---|---|
| 1ST TIME | 0.62 |
| 2ND TIME | 0.63 |
| 3RD TIME | 0.57 |
| 4TH TIME | 0.60 |
| 5TH TIME | 0.69 |
| AVERAGE | 0.62 |

CORNEAL ENDOTHELIAL CELL PHOTOGRAPHING APPARATUS

CROSS-REFERENCE TO RELATED APPLICATIONS

This application is based upon and claims the benefit of priority from the prior Japanese Patent Applications No. 2010-223124 filed on Sep. 30, 2010 and No. 2011-188642 filed on Aug. 31, 2011, the entire contents of which are incorporated herein by reference.

TECHNICAL FIELD

The present invention relates to a corneal endothelial cell photographing apparatus for photographing corneal endothelial cell images of an examinee's eye.

BACKGROUND ART

Heretofore, there is known an apparatus arranged to irradiate illumination light from an illumination light source toward a cornea and receive reflection light from the cornea through an imaging element (an image pickup element) to obtain an image of corneal endothelial cells in non-contact relation.

As an apparatus of this type, for example, there are known an apparatus provided with a focus detecting sensor for detecting a focus state with respect to corneal endothelium and arranged to move an apparatus main unit to a focus position of the endothelium and then take photographs (see JP 8(1996)-206080A) and an apparatus arranged to consecutively take photographs while moving an apparatus main unit in a predetermined direction (JP 7(1995)-79924A).

Meanwhile, the endothelial cells have to be observed at high powers (magnifications). Thus, high alignment accuracy is demanded. As an alignment detecting sensor for detecting alignment marks or indexes projected on a cornea, for example, a position sensor (PSD) is conventionally used. The positional information in an X direction and the positional information in a Y direction output from the position sensor are detected respectively to perform alignment (see FIGS. 10A and 10B).

DISCLOSURE OF THE INVENTION

Problems to be Solved by the Invention

In the above configuration, however, light receiving signals are obtained in the X direction and the Y direction separately when the alignment marks are photo-received (see FIG. 10A). It is therefore difficult to distinguish disturbance light and the alignment mark light when the disturbance light enters. If reflection light from an eyelid and eyelashes enters, for instance, a light receiving signal as shown in FIG. 10B is output, resulting in difficulty in detecting an alignment state in the X and Y directions. If a plurality of dot marks, a two-dimensional pattern image (e.g., a ring image), and others are photo-received, it is similarly difficult to specify that mark image and detect its position. Further, since an imaging range is narrow, the position of an examinee's eye may be lost if the eye greatly moves. Thus, alignment could not be performed by tracking the movement of the eye.

In other words, the information available for obtaining good endothelial cell images is limited and therefore the conventional alignment detecting sensor is likely to be unable to photograph good cell images.

The present invention has been made in consideration of the above problems and has a purpose to provide a corneal endothelial cell photographing apparatus capable of reliably obtaining an endothelial cell image of an examinee's eye.

Means of Solving the Problems

To achieve the above purpose, one aspect of the invention provides a corneal endothelial cell photographing apparatus comprising: an apparatus main unit including an illumination optical system for irradiating illumination light from an illumination light source to a cornea of an examinee's eye from an oblique direction and an imaging optical system for obtaining a corneal endothelial cell image by receiving reflection light from the cornea including corneal endothelial cells by a first imaging element; an anterior segment observation optical system including a second imaging element different from the first imaging element, the anterior segment observation optical system being adapted to pick up an anterior segment image of the examinee's eye by the second imaging element to observe the anterior segment image from front; a controller adapted to turn on the illumination light source and obtain a plurality of picked-up images output from the first imaging element; and an alignment detecting unit adapted to detect an alignment state of the main unit with respect to the examinee's eye based on a picked-up image output from the second imaging element during obtaining of the picked-up images by the controller.

BRIEF DESCRIPTION OF THE DRAWINGS

FIG. 9 is a table showing measurement results of returning time of alignment in X and Y directions.

MODE FOR CARRYING OUT THE INVENTION

Figure 1:
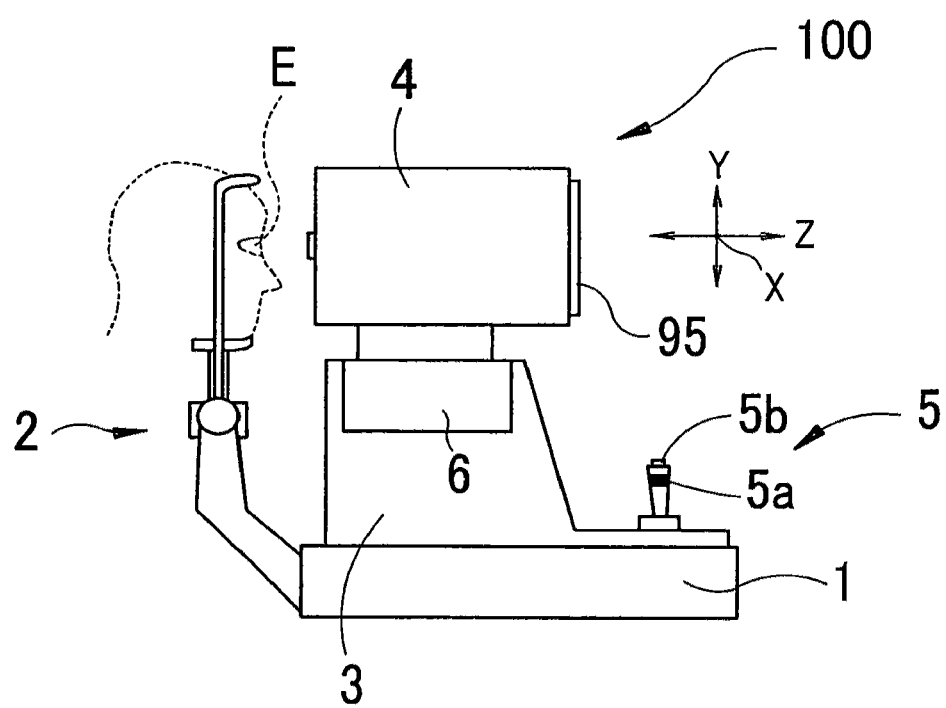
FIG. 1 is an external side configuration view of a corneal endothelial cell photographing apparatus in a preferred embodiment.

A detailed description of a preferred embodiment of the present invention will now be given referring to the accompanying drawings. FIG. 1 is an external side configuration view of a corneal endothelial cell photographing apparatus in the present embodiment.

An apparatus 100 is a so-called stationary apparatus, including a base 1, a head support unit 2 attached to the base 1, a movable unit 3 provided movably on the base 1 by a slide mechanism not shown, and a photographing part (a main unit) 4 that is provided movably with respect to the movable unit 3 and contains a photographing system and an optical system, which will be mentioned later.

The photographing part 4 is moved in a right and left direction (X direction), an up and down direction (Y direction), and a back and forth direction (Z direction) relative to an examinee's eye E by an XYZ drive part 6 provided in the movable unit 3. The movable unit 3 is moved in the X and Z directions by operation of a joystick 5. Further, when an examiner rotates a rotating knob 5a, the photographing part 4 is moved in the Y direction by Y-direction driving of the XYZ drive part 6. A start switch 5b is provided at a top of the joystick 5. A display monitor 95 is provided on an examiner side of the photographing part 4. In the present embodiment, the photographing part 4 is moved relative to the eye E by the slide mechanism not shown or the XYZ drive part 6.

Figure 2:
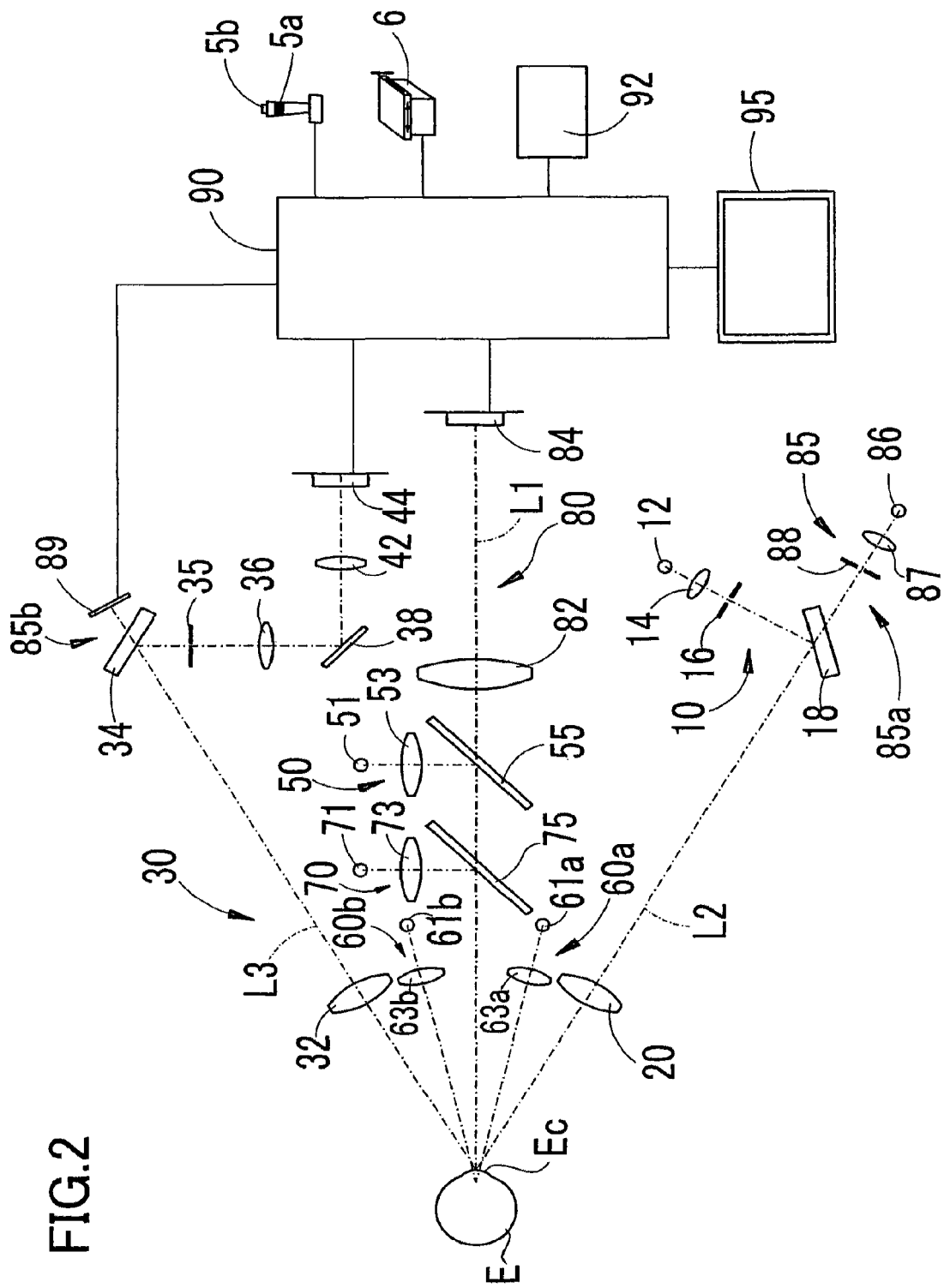
FIG. 2 is a schematic configuration view showing one example of an optical arrangement of an optical system contained in a photographing part, seen from above, and a configuration of a control system.
Figure 3:
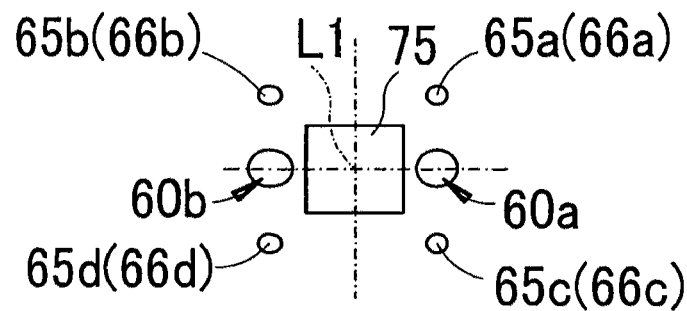
FIG. 3 is a view of a first projecting optical system and a second projecting optical system seen from an examinee side.

FIG. 2 is a schematic configuration view showing an example of an optical arrangement of an optical system contained in the photographing part 4, seen from above, and a configuration of a control system. FIG. 3 is a diagram of a first projecting optical system and a second projecting optical system seen from an examinee side. An entire structure of the optical system includes an illumination optical system 10 for irradiating illumination light from an illumination light source 12 toward a cornea Ec from an oblique direction, an imaging optical system 30 for obtaining an endothelial cell image by receiving reflection light from the cornea Ec including endothelial cells by a first imaging element 44, a front projecting optical system 50 for projecting alignment marks (indexes) from front toward the central portion of the cornea Ec, first projecting optical systems 60a and 60b for projecting infinite alignment marks toward the cornea Ec from an oblique direction, second projecting optical systems 65a to 65d (see FIG. 3) for respectively projecting finite alignment marks toward a peripheral part of the cornea Ec from different plural oblique directions, an internal fixation optical system 70 for projecting a fixation target from the inside with respect to the eye E, an anterior segment observation optical system 80 for observing an anterior segment image from front, and a Z alignment detection optical system 85 for detecting an alignment state of the photographing part 4 relative to the eye E in the Z direction. Each concrete configuration will be explained below.

The illumination optical system 10 includes an illumination light source (e.g., a visible LED, a flash lamp) 12 that emits visible light for photographing an endothelium, a condenser lens 14, a slit plate 16, a dichroic mirror 18 that reflects visible light and transmits infrared light, and a light projection lens 20. Light emitted from the illumination light source 12 illuminates the slit plate 16 via the condenser lens 14. Slit light having passed through the slit plate 16 is converged by the light projection lens 20 via the dichroic mirror 18 and is irradiated to the cornea. Herein, the slit plate 16 is located in a substantially conjugate position with the cornea Ec relative to the light projection lens 20.

The imaging optical system 30 and the illumination optical system 10 are horizontally symmetrical to each other with respect to an optical axis L1. The imaging optical system 30 includes an objective lens 32, a dichroic mirror 34 that reflects visible light and transmits infrared light, a mask 35, a first image forming lens 36, a total reflection mirror 38, a second image forming lens 42, and a first two-dimensional imaging element (e.g., two-dimensional CCD, CMOS, etc.) 44 to be used for obtaining an endothelial cell image. The mask 35 is placed in a substantially conjugate position with the cornea Ec relative to the objective lens 32. The first image forming lens 36 and the second image forming lens 42 constitute an image forming optical system to form an endothelial cell image on the imaging element 44. The imaging element 44 is placed in a substantially conjugate position with the cornea Ec through a lens system of the imaging optical system 30.

Corneal reflection light by the illumination optical system 10 travels in a direction of an optical axis L3 (in an oblique direction) and is converged by the objective lens 32. The light is then reflected by the dichroic mirror 34 to form an image on the mask 35 once whereby blocking the light which will be noise in obtaining an endothelial cell image. Light having passed through the mask 35 travels through the first image forming lens 36, the total reflection mirror 38, and the second image forming lens 42 and then forms an image on the two-dimensional imaging element 44. In this way, a corneal endothelial cell image at high powers (magnifications) is obtained. Output of the imaging element 44 is connected to a controller 90 and the obtained cell image is stored in a memory 92. The cell image is also displayed on the monitor 95.

The front projecting optical system 50 includes an infrared light source 51, a light projection lens 53, and a half mirror 55 to project infrared light for XY alignment detection onto the cornea Ec from an observation optical axis L1 direction. Infrared light emitted from the light source 51 is converted into parallel light by the light projection lens 53 and then is reflected by the half mirror 55. The reflected light is projected onto the central portion of the cornea Ec, forming a mark i10 (see FIG. 4B).

The first projecting optical systems 60a and 60b are placed respectively obliquely at predetermined angles with respect to the optical axis L1. The first projecting optical systems 60a and 60b include respectively infrared light sources 61a and 61b and collimator lenses 63a and 63b and are placed to be horizontally symmetrical to each other with respect to the optical axis L1 to project infinite marks to the eye E (see FIG. 2). The first projecting optical systems 60a and 60b are located on almost the same meridian as a horizontal plane passing the optical axis L1 (see FIG. 3).

Figure 4A:
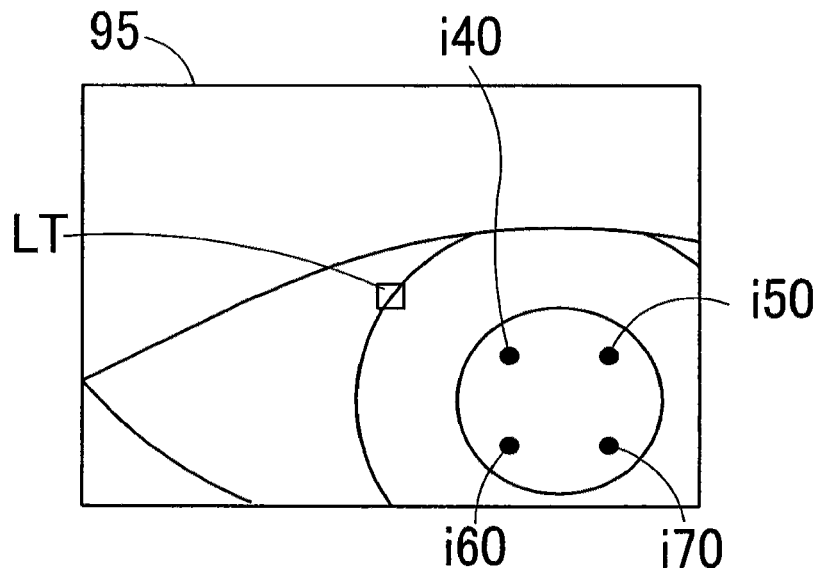
FIG. 4A is a view showing an example of an anterior segment observation screen in photographing an endothelium of a corneal central portion, which is a display example showing that misalignment is present.
Figure 4B:
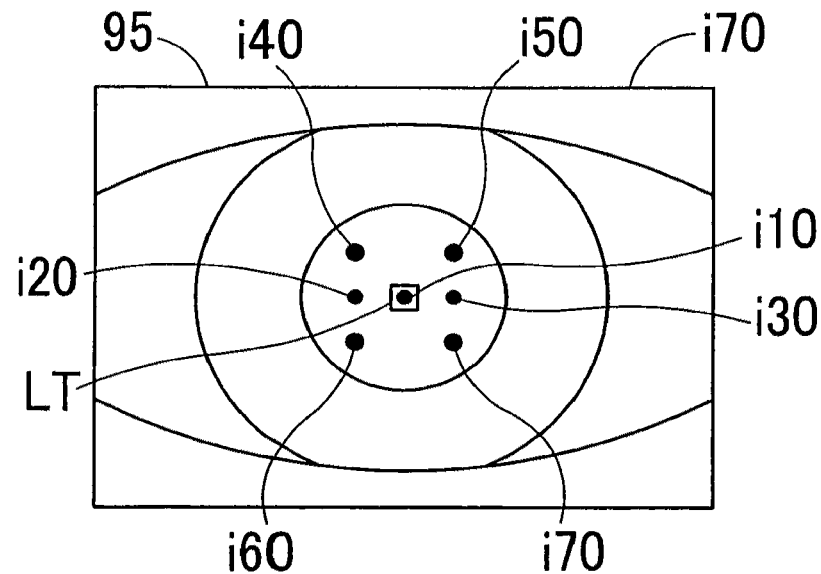
FIG. 4B is a view showing an example of the anterior segment observation screen in photographing the endothelium of the corneal central portion, which is a display example showing that an alignment state is proper.

Lights emitted from the light sources 61a and 61b are collimated respectively through the collimator lenses 63a and 63b and then projected onto the cornea Ec, forming marks i20 and i30 (see FIG. 4B).

The second projecting optical systems 65a to 65d are located respectively obliquely with respect to the optical axis L1. The second projecting optical systems 65a to 65d include respectively infrared light sources 66a to 66d and are placed to be horizontally symmetrical to each other with respect to the optical axis L1 to project finite marks onto the eye E. It is to be noted that the second projecting optical systems 65a and 65b are placed above the optical axis L1 and located on the same height in the Y direction. The second projecting optical systems 65c and 65d are placed below the optical axis L1 and located on the same height in the Y direction. The second projecting optical systems 65a and 65b are placed to be vertically symmetrical to the second projecting optical systems 65c and 65d with respect to the optical axis L1.

Herein, lights from the light sources 66a and 66b are irradiated obliquely from above toward the cornea Ec, forming marks i40 and i50 which are virtual images of the light sources 66a and 66b. Lights from the light sources 66c and 66d are irradiated obliquely from below toward the cornea Ec, forming marks i60 and i70 which are virtual images of the light sources 66c and 66d (see FIGS. 4A and 4B).

According to the above mark projecting optical systems, the mark i10 is formed at a corneal vertex of the eye E (see FIG. 4B). The marks i20 and i30 by the first projecting optical systems 60a and 60b are formed symmetrically to each other with respect to the mark i10 in the same horizontal positions as the mark i10. Further, the marks i40 and i50 by the second projecting optical systems 65a and 65b are formed above the mark i10 and horizontally symmetrically to each other with respect to the mark i10. The marks i60 and i70 by the second projecting optical systems 65c and 65d are formed below the mark i10 and horizontally symmetrically to each other with respect to the mark i10.

The internal fixation optical system 70 includes a visible light source (a fixation lamp) 71, a light projection lens 73, and a dichroic mirror 75 that reflects visible light and transmits infrared light to project light onto the eye E to make the eye E gaze forward. Visible light emitted from the light source 71 is converted into parallel light by the light projection lens 73, and then reflected by the dichroic mirror 75 and projected onto the fundus of the eye E. An external fixation optical system not shown is placed near the first projecting optical system and the second projecting optical system.

Return to FIG. 2. The anterior segment observation optical system 80 includes an objective lens 82 and a two-dimensional imaging element 84 to obtain an anterior segment front image. The imaging element 84 is a second imaging element different from the first imaging element 44. An anterior segment image and alignment marks are imaged by the second imaging element 84. As the two-dimensional imaging element 84, for example, a two-dimensional CCD image sensor (Charge coupled device image sensor) or a two-dimensional CMOS image sensor (Complementary Metal Oxide Semiconductor Image Sensor) is used.

The anterior segment illuminated by an anterior segment illumination light source not shown is imaged by the two-dimensional imaging element 84 through the dichroic mirror 75, the half mirror 55, and the objective lens 82. Similarly, a cornea reflection image formed by the front projecting optical system 50, the first projecting optical systems 60a and 60b, and the second projecting optical systems 65a to 65d is photo-received by the two-dimensional imaging element 84.

Output of the imaging element 84 is connected to the controller 90. As shown in FIGS. 4A and 4B, the monitor 95 displays the anterior segment image picked up by the imaging element 84. A reticle LT electronically displayed on the monitor 95 represents a reference of XY alignment. The observation optical system 80 is also used as a detection optical system for detecting an alignment state (a direction of alignment deviation (misalignment)/an amount of deviation) of the photographing part 4 with respect to the eye E.

The Z alignment detecting optical system 85 includes a light projecting optical system 85a for projecting light for detection toward the cornea Ec from an oblique direction and a light receiving optical system 85b for photo-receiving cornea reflection light projected by the light projecting optical system 85a. The optical axis L2 of the light projecting optical system 85a and the optical axis L3 of the light receiving optical system 85b are located to be horizontally symmetrical to each other with respect to the observation optical axis L1.

The light projecting optical system 85a includes, for example, an illumination light source 86 that emits infrared light, a condenser lens 87, a pinhole plate 88, and the lens 20. Herein, the pinhole plate 88 is located in a substantially conjugated position with the cornea Ec relative to the lens 20. The light receiving optical system 85b includes, for example, the lens 32 and a one-dimensional light receiving element (a line sensor) 89. Herein, the one-dimensional light receiving element 89 is located in a substantially conjugated position with the cornea Ec relative to the lens 32.

Infrared light emitted from the light source 86 illuminates the pinhole plate 88 through the condenser lens 87. Light having passed through an aperture of the pinhole plate 88 is projected onto the cornea Ec through the lens 20. The cornea reflection light is received by the light receiving element 89 through the lens 32 and the dichroic mirror 34.

Output of the light receiving element 89 is connected to the controller 90 and used for detecting Z alignment of the photographing part 4 with respect to the eye E. Herein, alignment light received by the light receiving element 89 changes its position according to a positional relationship in the Z direction between the photographing part 4 and the eye E. For instance, the controller 90 detects the position of the cornea reflection light based on a detection signal from the light receiving element 89 and thus detects an alignment state in the Z direction. It is to be noted that alignment detection using the light receiving element 89 is used for accurate alignment of the photographing part 4 with respect to the eye E.

The controller 90 performs control of the entire apparatus 100. The controller 90 is connected to the rotating knob 5a, the start switch 5b, the XYZ drive part 6, the two-dimensional imaging elements 44 and 84, each light source, the memory 92 serving as storage means, and the monitor 95.

For instance, the controller 90 controls display of the monitor 95. The controller 90 further detects the alignment state of the photographing part 4 with respect to the eye E in the XYZ directions based on light reception results of the alignment marks. Then, the controller 90 outputs a command signal to move the photographing part 4 based on a detection result. The controller 90 further detects the alignment state of the photographing part 4 in the Z direction with respect to the eye E based on a light reception result of the light receiving element 89.

Operations of the apparatus configured as above will be explained below. In the apparatus 100, after XYZ alignment is performed, the photographing part 4 is moved forward and, during which, the endothelial cells are consecutively photographed multiple times (multiple images). Details of each operation will be explained below.

<XYZ Alignment>

FIGS. 4A and 4B are diagrams showing examples of an anterior segment observation screen when the endothelium of the central portion of the cornea is to be photographed. Specifically, FIG. 4A is a display example showing that misalignment is present and FIG. 4B is a display example that an alignment state is proper. In this case, the light source 71 is turned on to direct the fixation direction of the eye E to the front. The examiner instructs the examinee to fix his/her gaze on the fixation target. While observing the anterior segment image displayed on the monitor 95, the examiner performs alignment of the photographing part 4 with respect to the eye E.

When rough alignment is performed as above (manual alignment by the examiner until the marks i40, i50, i60, i70 appear on the monitor 95), a corneal mark image by diffusion light is detected on a light receiving surface of the imaging element 84 as shown in FIG. 4A. The controller 90 searches a luminescent spot from an upper left coordinate position of the image toward a lower right side on the screen. When the marks i40, i50, i60, and i70 are detected, the controller 90 detects the position of the detected luminescent spot.

The controller 90 detects the center position of a rectangle defined by the marks i40, i50, i60, and i70 as a substantial corneal vertex and thereby determines a direction of alignment deviation and/or an amount of deviation of the photographing part 4 with respect to the eye E in the XY directions. The controller 90 controls driving of the drive part 6 to move the photographing part 4 in the XY directions so that the alignment deviation falls within a predetermined alignment tolerance range (e.g., a range in which the mark i10 is detectable). This enables automatic alignment in a wide range.

When the photographing part 4 is moved as above and the mark i10 is detected, the controller 90 terminates the alignment using the aforementioned marks i40 to i70 and then performs alignment using the mark i10. Herein, the controller 90 distinguishes the mark i10 from the marks i40 to i70 based on their positional relationships.

The controller 90 detects a coordinate position of the mark i10 and thus determines the direction of alignment deviation and/or the amount of deviation of the photographing part 4 with respect to the eye E in the XY directions. The controller 90 then controls driving of the drive part 6 to move the photographing part 4 in the XY directions so that the alignment deviation falls within a predetermined alignment tolerance range (e.g., the mark i10 is located within the reticle LT).

When the mark i10 is detected as above, similarly, infinite marks i20 and i30 are detected. The controller 90 compares the interval between the marks i20 and i30 detected as above and the interval between the finite marks i60 and i70 to obtain the misalignment direction and/or the deviation amount in the Z direction (First Alignment Detection). The controller 90 causes the photographing part 4 to move in the Z direction so that the alignment deviation of the photographing part 4 with respect to the eye E in the Z direction falls within the predetermined alignment tolerance range (e.g., where a difference between the center luminescent point of the infinite marks i20 and i30 and the center luminescent point of the finite marks i60 and i70 is plus or minus of 1 pixel (about ±0.1 mm in terms of size)) (First Automatic Alignment).

In this case, the controller 90 determines the misalignment in the Z direction by utilizing the property that, in the case where the photographing part 4 is misaligned (deviated) in a working distance direction, the interval between the above infinite marks i20 and i30 hardly changes, whereas the image interval between the finite marks i60 and i70 changes (for the details, see JP6(1994)-46999A). Instead of the marks i60 and i70, the marks i40 and i50 may be utilized. Further, Z alignment may be detected based on a distance of a mark from the optical axis L1 (Mark height).

When the alignment state is judged to be proper in the first Z alignment detection, the controller 90 stops operations for the first automatic alignment and starts second Z alignment detection using the detecting optical system 85 and second automatic alignment based on a detection result of the second Z alignment detection.

The controller 90 turns on the light source 86 to project alignment light onto the cornea Ec (the light source 86 may be turned on in advance) and detects its cornea reflection light through the light receiving element 89. The controller 90 controls driving of the drive part 6 based on a light reception result from the light receiving element 89 to move the photographing part 4 in the Z direction.

Figure 5:
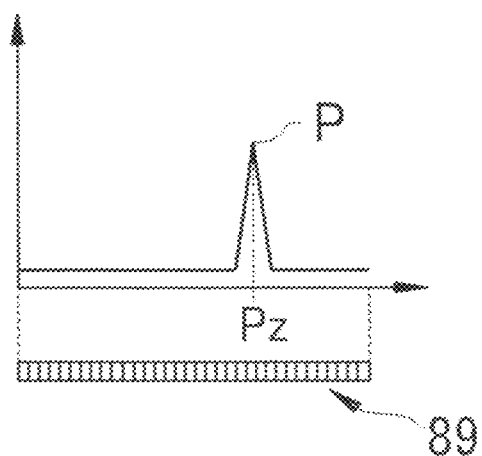
FIG. 5 is a diagram showing an example of accurate alignment detection.

For instance, the controller 90 detects a peak P corresponding to the reflection light from the corneal epithelium based on the light receiving signal output from the light receiving element 89 and thus detects an epithelium peak position Pz on the light receiving element 89 (see FIG. 5). The controller 90 then drives the drive part 6 so that the peak of the light receiving signal by the reflection light from the epithelium comes to a predetermined position (e.g., a center position) on the light receiving element 89.

When the alignment state in the XYZ directions by the aforementioned alignment operations meet a condition of alignment completion, the controller 90 judges that the alignment has been successfully completed in the XYZ directions.

<Photographing of Endothelial Cells>

Then, the controller 90 causes the illumination light source 12 to continuously light up and obtains a corneal endothelial cell image by visible illumination light at the two-dimensional imaging element 44. At that time, the controller 90 preferably causes the light source 12 to emit light with such a light intensity that allows epithelium reflection light to be detected but does not allow endothelium reflection light to be detected. The controller 90 continues to light up the light source 12 and controls driving of the drive part 6 to move forward the photographing part 4 toward the eye E. During movement of the photographing part 4 in the Z direction, the controller 90 continues the automatic alignment operation (tracking control using the imaging element 84) in the XY directions.

Figure 6:
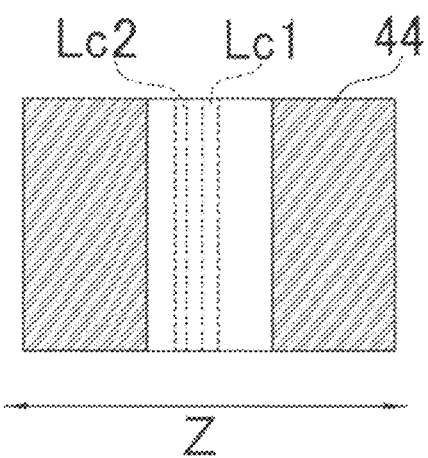
FIG. 6 is a diagram showing an example to determine a light receiving state of a cornea image based on an output image from an imaging element.

The controller 90 detects an output image from the imaging element 44 and controls the light source 12 and the drive part 6 based on a detection result thereof. FIG. 6 is a diagram showing one example to determine a light receiving state of a cornea image based on the image output from the imaging element 44. In FIG. 6, a central white rectangular region corresponds to an opening of the mask 35 placed in front of the imaging element 44 and right and left black hatched regions correspond to a light shielding part of the mask 35.

For instance, the controller 90 sets a first detection region Lc1 and a second detection region Lc2 each extending in a direction perpendicular to a thickness direction of the cornea (a Z direction in FIG. 6) in order to detect a light receiving state of the cornea image. The first detection region Lc1 is set to detect a light receiving state of the epithelium reflection light and the second detection region Lc2 is set to detect a light receiving state of the endothelium reflection light. The controller 90 calculates a sum SLC1 of luminance of all pixels in the first detection region Lc1 and also calculates a sum SLC2 of luminance of all pixels in the second detection region Lc2.

Figure 7A:
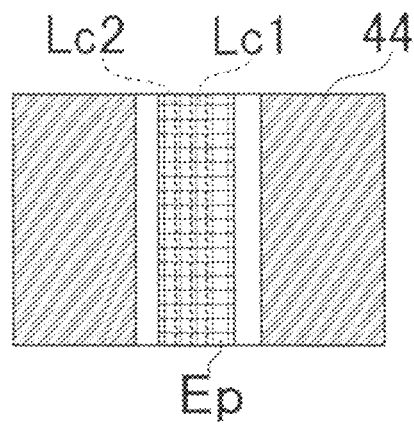
FIGS. 7A to 7C are diagrams showing changes in light receiving state of cornea reflection light while a photographing part is moved forward.
Figure 7B:
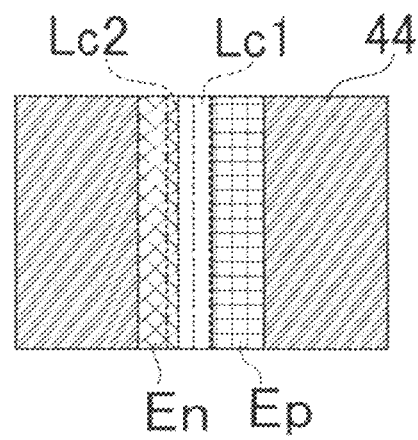
Figure 7C:
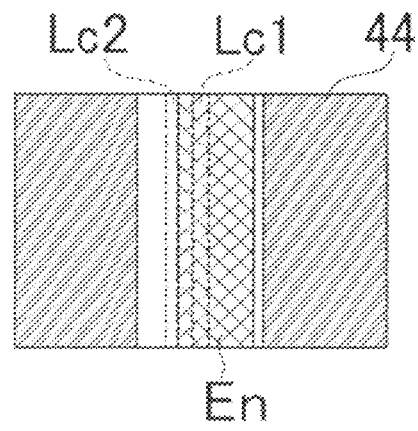
Figure 8A:
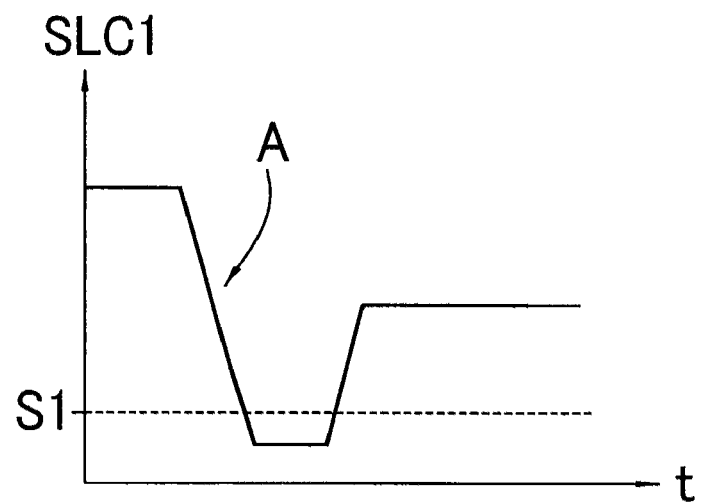
FIG. 8A is a time-series graph showing changes in sum SLC1 when the photographing part is moved forward.
Figure 8B:
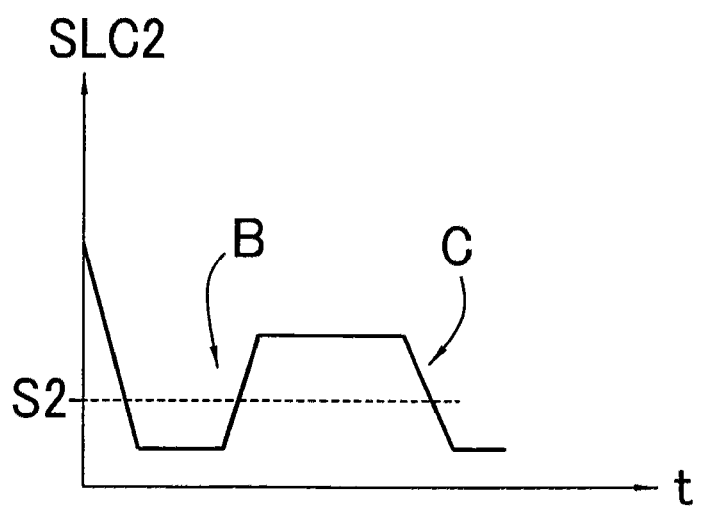
FIG. 8B is a time-series graph showing changes in sum SLC2 when the photographing part is moved forward.
Figure 10A:
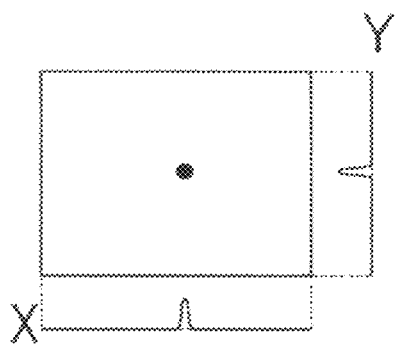
FIGS. 10A and 10B are explanatory diagrams to explain a configuration of a conventional corneal endothelial cell photographing apparatus.
Figure 10B:
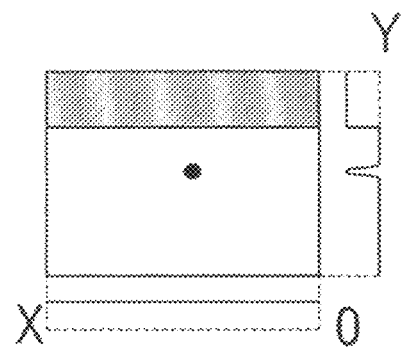

FIGS. 7A to 7C are diagrams showing changes in light receiving state of the cornea reflection light while the photographing part 4 is moved forward. FIGS. 8A and 8B are time-series graphs showing changes in the sums SLC1 and SLC2 while the photographing part 4 is moved forward. FIG. 8A corresponds to the sum SLC1 and FIG. 8B corresponds to the sum SLC2.

FIG. 7A is a diagram obtained when the alignment in the XYZ directions is completed. At that time, epithelium reflection light Ep is received on the first region Lc1. Therefore, the first sum SLC1 is calculated to be a high value corresponding to the epithelium reflection (see FIG. 8A).

As the photographing part 4 is moved forward, the epithelium reflection light Ep is moved rightward on the drawing sheets of FIGS. 7A to 7C. When the epithelium reflection light Ep goes across the detection region Lc1, the sum SLC1 greatly decreases (see an inclination A in FIGS. 7A and 8A). When the sum SLC1 decreases below a predetermined threshold S1, the controller 90 increases the light amount of the light source 12 to the degree that an endothelium image appears in the output image from the imaging element 44. Accordingly, the endothelium reflection light En is enabled to be detected by the imaging element 44.

After increasing the light amount of the light source 12, the controller 90 continues forward movement of the photographing part 4 and causes the memory 92 to successively stores images serially output from the imaging element 44. The two-dimensional imaging element 44 successively outputs imaging signals in combination with respective frame rates to the controller 90. Accordingly, the endothelial picked-up image is obtained multiple times (e.g., about 30 to 40 images) for 1 to 2 seconds. The controller 90 causes the memory 92 to store, as a stationary image, an image that satisfies a certain condition (e.g., an appropriate endothelial cell image has been obtained) out of output images. Thus, the endothelial cell image is photographed. In this case, the controller 90 may store in advance a predetermined number of images in the memory 92. The controller 90 then outputs the photographed image stored in the memory 92 to the monitor 95.

As the photographing part 4 is moved forward, the endothelium reflection light En is moved rightward in the image (see FIGS. 7A to 7C). When the endothelium reflection light En reaches the second detection region Lc2, the sum SLC2 increases (see an inclination B in FIG. 8B). While the endothelium reflection light En is received on the second detection region Lc2, a high value is kept. When the photographing part 4 is further moved and the endothelium reflection light En passes across the detection region Lc2, the sum SLC2 greatly decreases (see FIG. 7C and an inclination C in FIG. 8B). When the sum decreases below a predetermined threshold S2, the controller 90 darkens (including turning off) the light source 12 and stops driving of the drive part 6 to stop forward movement of the photographing part 4.

Techniques of continuously lighting up the light source 12 may include a technique of always lighting up the light source 12 and a technique of consecutively blinking the light source 12. In the case of consecutively blinking the light source 12, for example, the controller 90 causes the light source 12 to blink so that a plurality of endothelial images are obtained during movement of the photographing part 4. Further, the light source 12 may be blinked consecutively in sync with the frame rates of the two-dimensional imaging element 44. For instance, in the case where an imaging time of one image is 30 ms, the light source 12 is lighted up for several milliseconds from the start of image acquisition, and then is turned off. When acquisition of a next image is started, the light source 12 is turned on. In other words, those blinking operations are repeated.

Not limited to the above, the controller 90 may be adapted to control the light source 12 to emit light multiple times (of course, including continuous emission) to obtain a plurality of endothelial images by the imaging element 44.

<Tracking Control Using a Two-Dimensional Imaging Element Used for Anterior Segment Observation During Photographing>

While the endothelial cell images are continuously obtained as above, the eye E may move in the course thereof and thus an appropriate cell image may not be obtained. During obtaining picked-up images, therefore, the controller 90 detects the alignment state of the photographing part 4 with respect to the eye E based on the picked-up images output from the imaging element 84.

When an alignment detection result falls outside the alignment tolerance range (e.g., deviated by 0.25 mm or more in the X direction and 0.5 mm or more in the Y direction), the controller 90 controls driving of the drive part 6 to return the photographing part 4 to the proper alignment position. In other words, the controller 90 performs automatic alignment using the imaging element 84 for anterior segment observation.

For instance, the controller 90 detects the mark i10 in the picked-up image even after the light source 12 is turned on and detects an alignment deviation in the XY directions. When the detection result falls outside the predetermined alignment tolerance range, the controller 90 then controls driving of the drive part 6 to move the photographing part 4 in the XY directions so that the alignment deviation falls within the predetermined alignment tolerance range. Accordingly, even when the eye E is deviated from the proper alignment position, the photographing part 4 and the eye E are returned smoothly to an appropriate positional relationship. That is, the automatic tracking control during continuous acquisition of cell images is enabled.

The mark i10 is formed by parallel light from the front direction. Thus, if the photographing part 4 is greatly misaligned, the mark i10 is not photo-received by the imaging element 84. The controller 90 therefore detects the marks i40, i50, i60, and i70 in the picked-up image, thereby detecting an alignment deviation in the XY directions. The controller 90 then controls driving of the drive part 6 to move the photographing part 4 in the XY directions so that the alignment deviation falls within the predetermined alignment tolerance range. Accordingly, even if the eye E greatly deviates from the proper alignment position, the photographing part 4 and the eye E can be returned smoothly to the proper positional relationship, even though conventional automatic alignment using a position sensor could not return the photographing part 4 and the eye E thereto. That is, automatic tracking control is enabled in a wide range during continuous acquisition of cell images.

In the case of performing XY alignment using the two-dimensional imaging element 84 used for anterior segment observation as mentioned above, automatic tracking control is enabled in a wide range but the returning time is slower than in the case of using the position sensor. Therefore, there is a possibility that a predetermined number of endothelial cell images (e.g., about 30 to 40 images) could not be photographed within a predetermined time (e.g., about 1 to 2 seconds). Therefore, the returning time needed for the photographing part 4 to reach the proper alignment position in the present embodiment was investigated. To be concrete, the central luminescent points of the marks i40, i50, i60, and i70 were deviated by 3.2 mm (a detection limit range of the position sensor) from a proper position and the time needed to return to the proper position was measured. Results thereof are shown in FIG. 9. As is clear from FIG. 9, an average returning time is 0.62 seconds. It was confirmed that even when the eye E was greatly deviated from the alignment proper position, endothelial cells could be photographed sufficiently by a predetermined number of images (e.g., about 30 to 40 images) within a predetermined time (e.g., about 1 to 2 seconds). Accordingly, even in the case where the eye E largely deviates from the proper alignment position, which conventionally requires rephotographing, thus needing a long time to photograph endothelial cells, such rephotographing is not required and the photographing is completed in a short time. Thus, a burden on the examinee can be reduced.

When the above automatic tracking control is carried out, the controller 90 temporarily stops the forward movement of the photographing part 4 and, after the photographing part 4 returns to the proper position, restarts the forward movement of the photographing part 4. The controller 90 continuously obtains cell images by use of the imaging element 44 until the position of the endothelial cell image on the imaging element 44 reaches a predetermined photographing termination position. Specifically, while the alignment returning control in the XY directions is carried out (until the main unit is returned to the alignment proper position), obtaining of cell images output from the imaging element 44 is interrupted. Accordingly, only good endothelial cell images can be obtained.

Further, it may be arranged such that the controller 90 detects eclipse of light caused by eyelid and eyelashes by use of the marks i40 and i50 formed on the upper part of the cornea and, based on a detection result thereof, determines an eyelid open state. For instance, when at least one of the marks i40 and i50 disappears from the imaging element 84 or eclipse of a part or parts of marks i40 and i50 is detected, the controller 90 judges that the illumination light and the reflection light for obtaining corneal endothelial images may be blocked by the eyelid and eyelashes and thus determines that the eyelid open state is insufficient. Accordingly, it is determined whether or not the eyelid open state of the eye E is proper while the cell images are continuously obtained. This determination result is associated with cell images obtained successively and is utilized for example in choosing cell images.

In the above returning control, the anterior segment observation optical system 80 has a wide imaging range (e.g., 11 mm long and 15 mm wide) that will include at least the pupil, iris, sclera (preferably, eyelid, eyelashes) of the eye E when the corneal central portion of the eye E coincides with the optical axis L1. In other words, the imaging range is wider than an imaging range (e.g., 6.4 mm long and 6.4 mm wide) of the position sensor used as a conventional alignment detection sensor.

At the same time when the endothelial images are continuously obtained by using the special imaging element, the alignment is detected by using the imaging element 84 of the observation optical system 80. Consequently, even if the alignment greatly falls outside a proper state, thus exceeding the detectable range of the position sensor, automatic alignment is activated. Accordingly, even when an eye does not hold fixation, an endothelial cell image can be reliably obtained.

Since the alignment marks are detected based on the picked-up image obtained by the two-dimensional imaging element 84, the alignment marks are obtained as two-dimensional image data. Even when a plurality of dot-shaped marks as shown in FIG. 3 or a two-dimensional pattern image such as a ring-like mark and a linear mark is projected onto the eye E, it is easy to specify each mark image by image processing and detect an alignment state by using each mark image. For instance, the mark images are discriminated based on the positional relationship between the marks, the shape of a mark pattern, and others. An eyelid open state can also be detected. Further, it is easy to discriminate between the alignment luminescent point and disturbance light.

<Automatic Tracking Control in Z Direction Using Light Receiving Element 89 During Photographing>

If the alignment in the XY directions largely falls outside a proper state while the above cell images are continuously obtained, the alignment in the Z direction also largely falls outside a proper state. The controller 90 therefore may be adapted to perform XY automatic alignment and alignment returning control in the Z direction. In this case, while the alignment returning control in the Z direction is carried out (until the main unit is returned to the proper alignment position), obtaining of the cell images output from the imaging element 44 is interrupted. Thus, only good endothelial cell images can be obtained.

The controller 90 obtains for example alignment positional information before the alignment state of the photographing part 4 with respect to the eye E falls outside the tolerance range, based on a light reception result of the light receiving element 89 and thereby controls driving of the drive part 6 to return the photographing part 4 to an original alignment position.

Herein, the controller 90 causes the memory 92 to store the alignment position in the Z direction obtained before the alignment deviation in the XY directions falls outside the tolerance range and further temporarily stops the forward movement by the drive part 6. At the same time with the XY automatic alignment or after completion of XY alignment, the controller 90 drives the drive part 6 based on the positional information stored in the memory 92 to move the photographing part 4 toward the alignment position defined before the alignment is displaced.

For example, the controller 90 detects the position of the alignment marks based on the imaging signal output from the imaging element 84 during acquisition of cell images and also detects the position of the epithelium peak on the light receiving element 89. At that time, the epithelium peak moves on the light receiving element 89 in association with the forward movement of the photographing part 4.

Herein, when the eye E moves and the XY alignment deviation detected by the imaging element 84 greatly falls outside the tolerance range, the controller 90 causes the memory 92 to store in advance the position of the epithelium peak obtained before (preferably immediately before) the alignment deviation falls outside the tolerance range. In this case, the data to be stored in the memory 92 may be a pixel position at which the peak is detected or an amount of deviation between a predetermined position on the light receiving element 89 and a peak detected position.

In the case of performing returning operations, the controller 90 controls the drive part 6 to move the photographing part 4 in the XY directions so that the alignment deviation falls within the tolerance range as described above, the photographing part 4 is moved in the Z direction so that the epithelium peak on the light receiving element 89 is detected at the position (or its vicinity) stored in the memory 92.

When the above returning operation is completed, the controller 90 restarts the forward movement of the photographing part 4 and continuously obtains cell images by the imaging element 44 until the position of the epithelium peak on the light receiving element 89 reaches the predetermined photographing termination position.

It may be arranged such that the controller 90 turns off the light source 12 once when the alignment deviation falls outside the tolerance range and turns on the light source 12 again when the alignment deviation is detected to have reached the tolerance range. This makes it possible to reduce the burden on the examinee's eye due to the visible light source.

In the above explanation, the timing of misalignment is detected by use of the imaging element 84, but not limited thereto. When the eye E moves, a change of a peak position on the light receiving element 89 is different from that detected during forward movement of the photographing part 4.

Therefore, the controller 90 may be adapted to successively detect for example a change amount of the peak position per unit of time and, if the change amount falls outside a predetermined range, determine that misalignment occurs in the XY directions. Then, the controller 90 may perform returning control of the photographing part 4 with respect to the eye E based on the peak position on the light receiving element 89 obtained before misalignment occurs.

For alignment detection by the light receiving element 89, it may be arranged to detect a peak corresponding to endothelium reflection. Although the photographing part 4 is moved forward while cell images are continuously obtained, the image obtaining may also be conducted by moving the photographing part 4 backward. Further, the controller 90 may be adapted to activate automatic alignment in the Z direction using the imaging element 84 if the Z alignment is greatly displaced, in addition to the returning control using the light receiving element 89.

In the above configuration, the alignment state is detected by using the alignment marks. It is only necessary to detect alignment based on a imaging signal output from the imaging element. For instance, the controller 90 may be arranged to extract a characteristic portion (e.g., pupil, iris) of the anterior segment image and detect a positional deviation based on the extracted characteristic portion.

The above configuration uses the same two-dimensional imaging element for anterior segment observation and alignment detection, but is not limited thereto. Separate two-dimensional imaging elements may be provided for anterior segment observation and alignment detection. For instance, a light splitting member (e.g., a half mirror) may be placed between the lens 82 and the imaging element 84 and a two-dimensional imaging element for detecting alignment may be placed in a reflecting direction of the light splitting member.

Further, the present invention is not limited to the above embodiment and may be embodied in other specific forms without departing from the essential characteristics thereof.

The invention claimed is:

1. A corneal endothelial cell photographing apparatus comprising:
    an apparatus main unit including an illumination optical system for irradiating illumination light from an illumination light source to a cornea of an examinee's eye from an oblique direction and an imaging optical system for obtaining a corneal endothelial cell image by receiving reflection light from the cornea including corneal endothelial cells by a first imaging sensor;
    an anterior segment observation optical system including a second imaging sensor different from the first imaging sensor, the anterior segment observation optical system being adapted to pick up an anterior segment image of eye by the second imaging sensor to observe the anterior segment image from front;
    a controller adapted to turn on the illumination light source and obtain a plurality of picked-up images output from the first imaging sensor;
    an alignment detecting unit adapted to detect an alignment state of the main unit with respect to the examinee's eye based on a picked-up image output from the second imaging sensor during obtaining of the picked-up images by the controller; and
    a drive part for relatively moving the main unit with respect to the examinee's eye, wherein
        the corneal endothelial cell image (i) is formed on the first imaging sensor and (ii) is displayed on a monitor,
        the first imaging sensor is a two-dimensional imaging sensor, and
        when a detection result of the alignment detecting unit falls outside an alignment tolerance range, the controller drives the drive part to return the main unit to a proper alignment position.

2. The endothelial cell photographing apparatus according to claim 1, wherein
    after the detection result of the alignment detecting unit falls outside the alignment tolerance range, the controller interrupts obtaining of the picked-up images output from the first imaging sensor until the main unit is returned to the proper alignment position.

3. The endothelial cell photographing apparatus according to claim 1, further comprising an alignment mark projecting optical system for projecting an alignment mark toward the cornea,
    wherein the anterior segment observation optical system picks up the anterior segment image of the examinee's eye and the alignment mark by the second imaging sensor,
    the alignment detecting unit detects an alignment state of the main unit with respect to the examinee's eye based on the alignment mark of the picked-up image output from the second imaging sensor while the controller obtains the picked-up images.

4. The endothelial cell photographing apparatus according to claim 3, wherein
    the projecting optical system is a projecting optical system for projecting a plurality of marks toward the cornea of the examinee's eye,
    wherein the alignment detecting unit detects the alignment state based on each of the marks, and
    the controller performs automatic alignment based on each alignment detection result.

5. The endothelial cell photographing apparatus according to claim 4, further comprising a detecting optical system including a projecting optical system for projecting light for detection toward the cornea from an oblique direction and a light receiving optical system for receiving corneal reflection light by the projecting optical system by a light receiving sensor, the detecting optical system being adapted to detect an alignment state of the main unit in a back and forth direction with respect to the examinee's eye based on a light reception result of the light receiving sensor,
    wherein the controller obtains, based on the light reception result of the light receiving sensor, alignment positional information before the alignment state of the main unit with respect to the examinee's eye falls outside the tolerance range, and the controller controls driving of the drive part to return the main unit to an original alignment position.

6. A corneal endothelial cell photographing apparatus comprising:
    an apparatus main unit including an illumination optical system for irradiating illumination light from an illumination light source to a cornea of an examinee's eye from an oblique direction and an imaging optical system for obtaining a corneal endothelial cell image by receiving reflection light from the cornea including corneal endothelial cells by a first imaging sensor;
    an anterior segment observation optical system including a second imaging sensor different from the first imaging sensor, the anterior segment observation optical system being adapted to pick up an anterior segment image of the examinee's eye by the second imaging sensor to observe the anterior segment image from front;
    a controller adapted to turn on the illumination light source and obtain a plurality of picked-up images output from the first imaging sensor;
    an alignment detecting unit adapted to detect an alignment state of the main unit with respect to the examinee's eye based on a picked-up image output from the second imaging sensor; and
    a drive part for relatively moving the main unit with respect to the examinee's eye, wherein
        the corneal endothelial cell image (i) is formed on the first imaging sensor and (ii) is displayed on a monitor,
        the first imaging sensor is a two-dimensional imaging sensor, and when a detection result of the alignment detecting unit falls outside an alignment tolerance range, the controller drives the drive part to return the main unit to a proper alignment position.

7. The endothelial cell photographing apparatus according to claim 6,
wherein the optical system and the imaging a corneal endothelium are placed independently from the optical system and the imaging sensor for imaging an anterior segment so that the respective optical elements are not commonly used.

* * * * *